(12) United States Patent
Shoji

(10) Patent No.: US 9,346,826 B2
(45) Date of Patent: *May 24, 2016

(54) PROCESS FOR PRODUCING AN INTERMEDIATE FOR A CYCLIC CARBODIIMIDE COMPOUND

(75) Inventor: Shinichiro Shoji, Iwakuni (JP)

(73) Assignee: TEIJIN LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/704,093

(22) PCT Filed: Jun. 15, 2011

(86) PCT No.: PCT/JP2011/064194
§ 371 (c)(1),
(2), (4) Date: Dec. 13, 2012

(87) PCT Pub. No.: WO2011/158959
PCT Pub. Date: Dec. 22, 2011

(65) Prior Publication Data
US 2013/0085273 A1  Apr. 4, 2013

(30) Foreign Application Priority Data

Jun. 16, 2010 (JP) ................... 2010-137202
Jun. 16, 2010 (JP) ................... 2010-137203

(51) Int. Cl.
*C07C 213/02* (2006.01)
*C07C 217/84* (2006.01)
*C07D 498/10* (2006.01)

(52) U.S. Cl.
CPC ............ *C07D 498/10* (2013.01); *C07C 213/02* (2013.01)

(58) Field of Classification Search
CPC ... C07C 213/02; C07C 217/84; C07D 498/10
USPC .......................................... 564/417; 540/453
See application file for complete search history.

(56) References Cited

U.S. PATENT DOCUMENTS

| 4,870,206 | A | 9/1989 | Sanders et al. |
| 5,294,742 | A | 3/1994 | Schach et al. |
| 2004/0209946 | A1 | 10/2004 | Yin et al. |
| 2011/0224385 | A1 | 9/2011 | Shoji et al. |
| 2011/0251384 | A1 | 10/2011 | Shoji et al. |

FOREIGN PATENT DOCUMENTS

| JP | 58-4750 | A | 1/1983 |
| JP | 62-39549 | A | 2/1987 |
| JP | 1-29349 | A | 1/1989 |
| JP | 6-41026 | A | 2/1994 |
| JP | 2004-332166 | A | 11/2004 |
| JP | 2005-350829 | A | 12/2005 |
| WO | 2010/071211 | A1 | 6/2010 |
| WO | 2010/071213 | A1 | 6/2010 |

OTHER PUBLICATIONS

International Preliminary Report on Patentability for Application No. PCT/JP2011/064194 issued Jan. 15, 2013.
Laliberte et al.; Molecular Tectonics. Porous Hydrogen-Bonded Networks Built from Derivatives of Pentaerythrityl Tetraphenyl Ether; J. Org. Chem., 2004, vol. 69, pp. 1776-1787.

*Primary Examiner* — Bruck Kifle
(74) *Attorney, Agent, or Firm* — Sughrue Mion, PLLC

(57) ABSTRACT

A process for producing an intermediate for a cyclic carbodiimide compound includes a process for producing an amine compound represented by the following formula (B), comprising the step of reducing a nitro compound represented by the following formula (A) and containing a compound having a haloarene skeleton in the presence of a metal catalyst and a basic compound. The process also includes a process for producing a thiourea compound, including the step of reacting an amine compound represented by the formula (B) with carbon disulfide in the presence of imidazole.

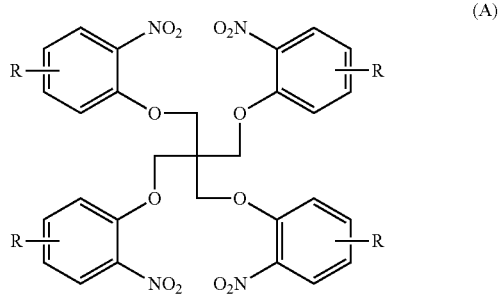

(A)

(R is a hydrogen atom or an alkyl group having 1 to 6 carbon atoms.)

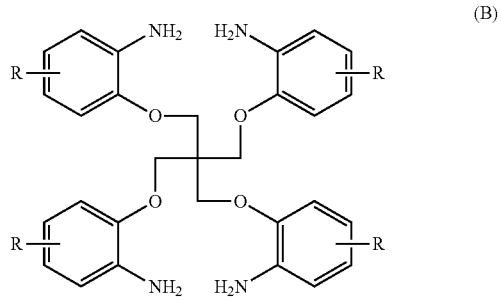

(B)

(R is as defined in the above formula (A).).

5 Claims, No Drawings

PROCESS FOR PRODUCING AN INTERMEDIATE FOR A CYCLIC CARBODIIMIDE COMPOUND

TECHNICAL FIELD

The present invention relates to a process for producing an amine compound or a thiourea compound which is useful as an intermediate for a cyclic carbodiimide compound.

BACKGROUND ART

Since the hydrolysis of a compound having an ester bond such as a polyester is promoted by a polar group such as a carboxyl group, it is proposed to reduce the concentration of the carboxyl group by using a sealing agent for a carboxyl group (Patent Document 1, Patent Document 2). A carbodiimide compound is used as the sealing agent for a carboxyl group.

However, since this carbodiimide compound is a linear compound, a volatile isocyanate compound is by-produced during use and generates a bad odor, thereby deteriorating work environment.

Then, the inventors of the present invention found as the sealing agent a cyclic carbodiimide compound which does not by-produce an isocyanate compound when it reacts with a carboxyl group and filed an international application (Patent Document 3). However, industrial processes for producing this useful cyclic carbodiimide compound and an intermediate therefor have not been established.

(Patent Document 1) JP-A 2004-332166
(Patent Document 2) JP-A 2005-350829
(Patent Document 3) PCT/JP2009/071190

DISCLOSURE OF THE INVENTION

It is an object of the present invention to improve the reaction yield of an amine compound represented by the following formula (B) when it is synthesized by reducing a nitro compound represented by the following formula (A) in the presence of a metal catalyst.

The inventors of the present invention investigated means of improving the reaction yield of the amine compound represented by the following formula (B) when it is synthesized by reducing the nitro compound represented by the following formula (A) in the presence of a metal catalyst.

As a result, they found that the nitro compound represented by the following formula (A) which is a raw material for the production of the amine compound contains a compound having a haloarene skeleton as an impurity derived from its production process and that the yield of the amine compound is reduced by this compound having a haloarene skeleton. They also found that the yield is remarkably improved when a basic compound capable of capturing a dehalogenating component such as hydrogen halide is existent during a reaction. The present invention was accomplished based on these findings.

When the dehalogenating component is existent in the reaction system as it is, the decomposition of the nitro compound and the amine compound is promoted with the result that the yield of the amine compound drops. However, when the basic compound is existent, the dehalogenating component is captured and there exists no free dehalogenating component in the reaction system, thereby making it possible to greatly suppress the decomposition of the nitro compound and the amine compound.

It is another object of the present invention to provide a process for producing a thiourea compound represented by the following formula (C) from the obtained amine compound represented by the formula (B).

The inventors found that the yield of the thiourea compound represented by the formula (C) is remarkably improved by making imidazole existent when it is synthesized by reacting the amine compound represented by the formula (B) with carbon disulfide. The present invention was accomplished based on this finding.

That is, the present invention includes the following inventions.

1. A process for producing an amine compound represented by the following formula (B), comprising the step of reducing a nitro compound represented by the following formula (A) and containing a compound having a haloarene skeleton in the presence of a metal catalyst and a basic compound.

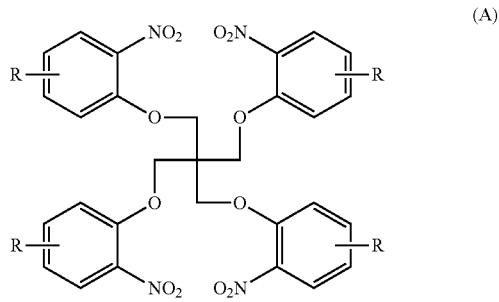

(R is a hydrogen atom or an alkyl group having 1 to 6 carbon atoms.)

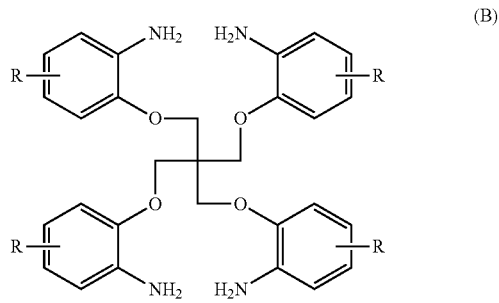

(R is as defined in the above formula (A).)

2. The production process in the above paragraph 1, wherein the metal catalyst is at least one selected from the group consisting of palladium, ruthenium, platinum, rhodium, nickel, copper, metal oxides thereof, metal hydroxides thereof and metal-supported catalysts obtained by precipitating any one of them on a carrier selected from activated carbon, alumina, titania and silica.

3. The production process in the above paragraph 1, wherein the basic compound is triethylamine.

4. A process for producing a thiourea compound represented by the following formula (C), comprising the step of reacting the amine compound represented by the formula (B) and obtained by the process in the above paragraph 1 with carbon disulfide in the presence of imidazole.

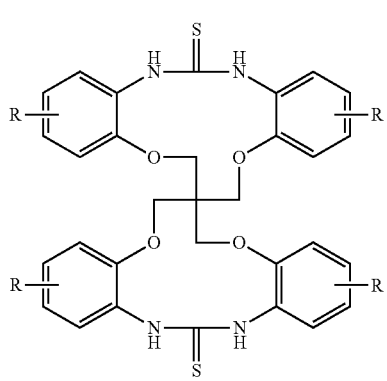

(R is a hydrogen atom or an alkyl group having 1 to 6 carbon atoms.)

5. The production process in the above paragraph 4, wherein methyl ethyl ketone is used as a reaction solvent.

BEST MODE FOR CARRYING OUT THE INVENTION

<Production Process of Amine Compound>

The present invention is a process for producing an amine compound represented by the following formula (B), comprising the step of reducing a nitro compound represented by the following formula (A) and containing a compound having a haloarene skeleton in the presence of a metal catalyst and a basic compound.

(Nitro Compound)

The nitro compound is represented by the following formula (A).

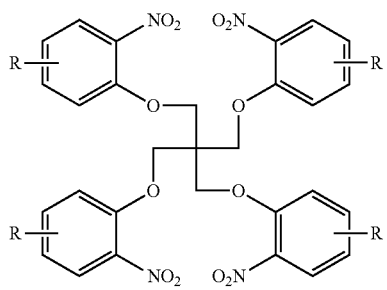

In the above formula (A), R is a hydrogen atom or an alkyl group having 1 to 6 carbon atoms. Examples of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group.

The compound having a haloarene skeleton is a monocyclic or polycyclic aromatic hydrocarbon compound having at least one halogen atom. Examples of the monocyclic aromatic hydrocarbon compound include halogenated benzene and halogenated nitrobenzene. Examples of the polycyclic aromatic hydrocarbon compound include halogenated naphthalene and halogenated nitronaphthalene.

Since o-halogenated nitrobenzene such as o-chloronitrobenzene is used as a raw material to synthesize the nitro compound (A) at low cost, a compound similar to the nitro compound (A) and containing a halogen component or a halogenated aromatic hydrocarbon compound such as o-halogenated nitrobenzene is often contained in the nitro compound.

Although the effect of the present invention is confirmed without limiting the content of the compound having a haloarene skeleton in the nitro compound (A), from the viewpoint of the production cost of the amine compound, the content of the above compound is preferably 0.001 to 0.5 equivalent, more preferably 0.001 to 0.1 equivalent based on 1 equivalent of the nitro compound.

(Amine Compound)

The amine compound obtained by the production process of the present invention is represented by the following formula (B).

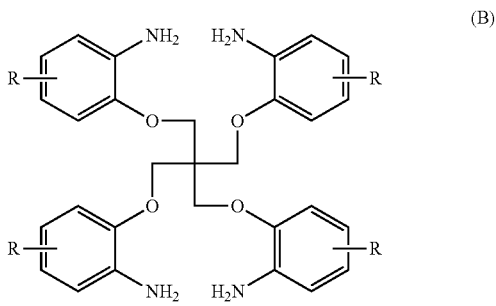

In the above formula (B), R is as defined in the above formula (A).

(Reaction)

The reaction is a reduction reaction of the nitro compound (A) by contacting a hydrogen gas in a solvent in the presence of a metal catalyst and a basic compound.

The reaction temperature is selected from a range from 25° C. to 150° C. When the reaction temperature is lower than 25° C., reactivity becomes unsatisfactory and the reaction may take a long time. When the reaction temperature is higher than 150° C., a side reaction different from the intended reaction such as a decomposition reaction may occur. From this point of view, the reaction temperature is preferably 50 to 120° C., more preferably 70 to 100° C.

Although the reaction proceeds at normal pressure, to promote the reaction, pressure is preferably applied. The pressure is selected from a range of 0.2 MPa or more. When the pressure is lower than 0.2 MPa, an effect may not be obtained from the application of pressure. From the viewpoint of equipment, the pressure is preferably in the range of 0.5 to 1.0 MPa.

The metal catalyst is preferably at least one selected from the group consisting of palladium, ruthenium, platinum, rhodium, nickel, copper, metal oxides thereof, metal hydroxides thereof and metal-supported catalysts obtained by precipitating any one of them on a carrier selected from activated carbon, alumina, titania and silica. Specific examples thereof include palladium carbon, palladium carbon-ethylenediamine complex, palladium-fibroin, palladium-polyethyleneimine, rhodium carbon, platinum oxide, nickel and copper. Activated carbon is preferably used as the carrier from the viewpoint of cost. The amount of the metal catalyst may be suitably set based on the weight of the nitro compound (A) to ensure that the reaction proceeds. When the amount of the metal catalyst is 0.05 wt % or more, the reaction fully proceeds. There is no upper limit but it may be 5 wt % or less from the viewpoint of balance with cost.

Examples of the basic compound include inorganic bases such as sodium carbonate, potassium carbonate and sodium hydrogen carbonate, and organic bases such as triethylamine, pyridine and imidazole. Triethylamine is particularly preferred from the viewpoints of cost and handling ease. The amount of the basic compound is 1 equivalent or more based on halogen equivalent contained in the nitro compound (A). When the amount of the basic compound is smaller than 1 equivalent, satisfactory capturing ability is not obtained and the purity of the amine compound (B) may lower. Although there is no upper limit, the amount of the basic compound is preferably 1 to 5 equivalents, more preferably 1 to 3 equivalents from the viewpoint of balance with cost.

Examples of the solvent include methanol, ethanol, isopropyl alcohol, dioxane, tetrahydrofuran, ethyl acetate, dichloromethane, chloroform, N,N-dimethylformamide, methyl ethyl ketone, acetone, toluene, acetonitrile and mixed solvents thereof.

A pressure reactor having stirring and heating functions is used as equipment.

<Production Process of Thiourea Compound>

The present invention includes a process for producing a thiourea compound represented by the following formula (C), comprising the step of reacting the amine compound represented by the formula (B) and obtained by the above process with carbon disulfide in the presence of imidazole.

(Amine Compound)

As described above, the amine compound can be produced by reducing a nitro compound represented by the formula (A) in the presence of a metal catalyst and a basic compound.

(Thiourea Compound)

The thiourea compound obtained by the production process of the present invention is represented by the following formula (C).

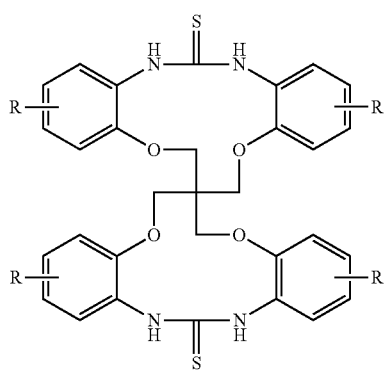

(C)

In the formula (C), R is a hydrogen atom or an alkyl group having 1 to 6 carbon atoms.

(Reaction)

The reaction is a reaction of the amine compound (B) in a solvent in the presence of carbon disulfide and imidazole. The weight ratio of the amine compound (B) and carbon disulfide may be suitably set to ensure that the reaction proceeds. When 2 equivalents or more of carbon disulfide is used based on 1 equivalent of the amine compound (A), the reaction fully proceeds. There is no upper limit but it may be 10 equivalents or less from the viewpoint of balance with cost. The weight ratio of the amine compound and imidazole may be also suitably set to ensure that the reaction proceeds. When 2 equivalents or more of imidazole is used based on 1 equivalent of the amine compound (B), the reaction fully proceeds. There is no upper limit but it may be 10 equivalents or less from the viewpoint of balance with cost.

The reaction temperature is selected from a range from 25° C. to 150° C. When the reaction temperature is lower than 25° C., reactivity becomes low and a satisfactory yield may not be obtained. When the reaction temperature is higher than 150° C., a side reaction different from the intended reaction such as a decomposition reaction may occur. From this point of view, the reaction temperature is preferably 50 to 100° C., more preferably 70 to 90° C. Although the reaction fully proceeds at normal pressure, it may be carried out under an increased pressure.

Examples of the solvent include methanol, ethanol, isopropyl alcohol, dioxane, tetrahydrofuran, ethyl acetate, dichloromethane, chloroform, N,N-dimethylformamide, methyl ethyl ketone, acetone, toluene and acetonitrile. Although the reaction may be carried out in any one of the above solvents, methyl ethyl ketone is preferably used from the viewpoints of the yield and purity of the obtained thiourea compound.

A reactor having stirring and heating functions which is combined with an apparatus for collecting hydrogen sulfide produced during the reaction is used as equipment.

EXAMPLES

Production Process of Amine Compound

1. The following examples are given to further illustrate the process for producing an amine compound. Physical properties were measured by the following methods.

(1) Identification of Amine Compound by NMR:

The synthesized amine compound was confirmed by $^1$H-NMR and $^{13}$C-NMR. JNR-EX270 of JEOL Ltd. was used for NMR. Heavy chloroform was used as a solvent. The purity of the amine compound was obtained from an integral value of $^1$H-NMR.

(2) Yield of Amine Compound:

The yield of the synthesized amine compound was obtained from the following equation by measuring the dry weight of the amine compound identified by NMR.

Yield of amine compound [%]=(dry weight of amine compound/molecular weight of amine compound)/number of moles of nitro compound)× 100×purity of amine compound [%]

Example 1

Synthesis of Amine Compound A1

N1 . . . compound of the formula (A) in which R=H

A1 . . . compound of the formula (B) in which R=H

A nitro compound N1 (0.1 mol) represented by the following formula and containing o-chloronitrobenzene (0.01 mol), 5% palladium carbon (Pd/C) (1.24 g), 62 ml of N,N-dimethylformamide and triethylamine (0.025 mol) were charged into an autoclave reactor having a stirring function, the inside of the autoclave reactor was substituted by nitrogen 3 times, and a reaction was carried out under agitation while 0.8 MPa hydrogen was always supplied at 90° C. and terminated when the amount of hydrogen did not decrease any more.

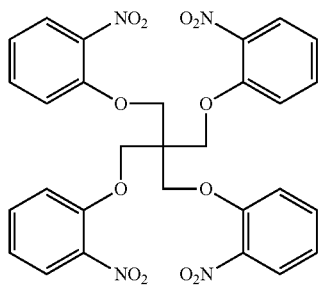 [SMILES: Nc1ccccc1OCC(COc1ccccc1N)(COc1ccccc1N)COc1ccccc1N]

The reaction solution from which Pd/C had been separated was added to 30% (v/v) methanol water in a weight ratio of 1:3 to be crystallized, and then the resulting product was collected by filtration to obtain a solid product. It was confirmed by NMR that the solid product was an amine compound A1 represented by the following formula.

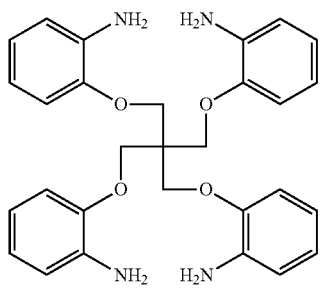

The yield of the amine compound A1 was 95.1%. The amine compound A1 was creamy white.

Comparative Example 1

Synthesis of Amine Compound A1

A nitro compound N1 (0.1 mol) represented by the following formula and containing o-chloronitrobenzene (0.01 mol), 5% palladium carbon (Pd/C) (1.24 g) and 62 ml of N,N-dimethylformamide were charged into an autoclave reactor having a stirring function, the inside of the autoclave reactor was substituted by nitrogen 3 times, and a reaction was carried out under agitation while 0.8 MPa hydrogen was always supplied at 90° C. and terminated when the amount of hydrogen did not decrease any more.

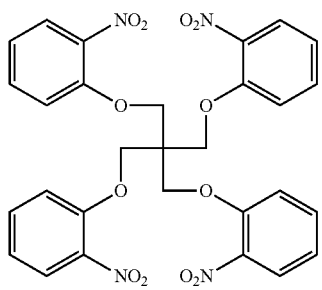

The reaction solution from which Pd/C had been separated was added to 30% (v/v) methanol water in a weight ratio of 1:3 to be crystallized, and then the resulting product was collected by filtration to obtain a solid product. It was confirmed by NMR that the solid product was an amine compound A1 represented by the following formula.

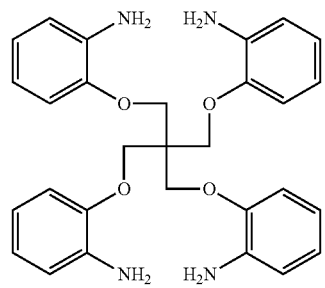

The yield of the amine compound A1 was 75.9%. The amine compound A1 was reddish brown.

<Production Process of Thiourea Compound>

The following examples are given to further illustrate the production of a thiourea compound. Physical properties were measured by the following methods.

(1) Identification of Thiourea Compound by NMR:

The synthesized thiourea compound was confirmed by $^1$H-NMR and $^{13}$C-NMR. JNR-EX270 of JEOL Ltd. was used for NMR. Heavy dimethyl sulfoxide was used as a solvent.

(2) Yield of Thiourea Compound:

The yield of the synthesized thiourea compound was obtained from the following equation by measuring the dry weight of the thiourea compound identified by NMR.

Yield of thiourea compound [%]=(dry weight of thiourea compound/molecular weight of thiourea compound)/number of moles of amine compound)×100[%]

Example 2

Synthesis of Thiourea Compound T1

A1 . . . compound of formula (A) in which R=H
T1 . . . compound of formula (B) in which R=H An amine compound A1 (0.025 mol) represented by the following formula, imidazole (0.15 mol), carbon disulfide (0.15 mol) and 60 ml of methyl ethyl ketone were charged into a reactor having a stirrer, a heater and a walter containing alkaline water in an $N_2$ atmosphere.

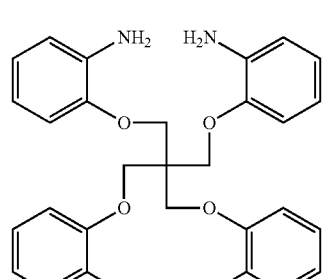

The reaction solution was heated at 80° C. to be reacted for 15 hours. A solid precipitated after the reaction was collected by filtration and washed with acetone to obtain a product. It was confirmed by NMR that the product was a thiourea compound T1 represented by the following formula.

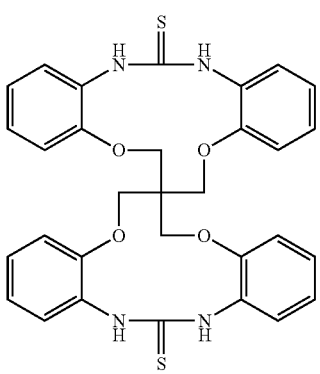 [SMILES: S=C1Nc2ccccc2OCC2(COc3ccccc3N1)COc1ccccc1NC(=S)Nc1ccccc1OC2]

The yield of the thiourea compound T1 was 89.4%.

Comparative Example 2

Synthesis of Thiourea Compound T1

An amine compound A1 (0.025 mol) represented by the following formula, triethylamine (0.2 mol), carbon disulfide (0.2 mol) and 60 ml of methyl ethyl ketone were charged into a reactor equipped with a stirrer, a heater and a walter containing alkaline water in an $N_2$ atmosphere. The reaction solution was heated at 80° C. to be reacted for 15 hours. A solid precipitated after the reaction was collected by filtration and washed with acetone to obtain a product. It was confirmed by NMR that the product was a thiourea compound T1 represented by the following formula.

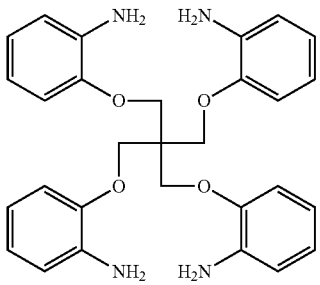

The yield of the thiourea compound T1 was 66.1%.

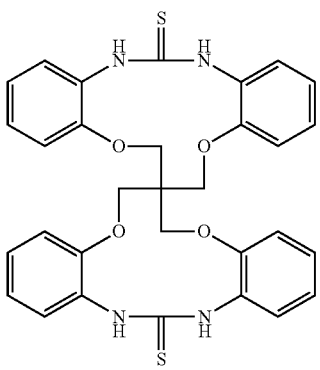 [SMILES: S=C1Nc2ccccc2OCC2(COc3ccccc3N1)COc1ccccc1NC(=S)Nc1ccccc1OC2]

Effect of the Invention

According to the production process of the present invention, a specific amine compound which is useful as an intermediate for a cyclic carbodiimide compound can be produced at a high yield. That is, according to the production process of the present invention, an amine compound (B) can be produced from a nitro compound (A) containing a compound having a haloarene skeleton at a high yield. Particularly, an amine compound (B) can be produced from a nitro compound (A) containing a halogenated aromatic compound having a plurality of halogenated aromatic rings at a high yield.

According to the production process of the present invention, a thiourea compound represented by the formula (C) which is useful as an intermediate for a cyclic carbodiimide compound can be produced at a high yield.

INDUSTRIAL APPLICABILITY

The amine compound and the thiourea compound obtained by the production processes of the present invention are useful as intermediates for a cyclic carbodiimide compound which is useful as a sealing agent for polyesters.

The invention claimed is:

1. A process for producing an amine compound represented by the following formula (B), comprising the step of reducing a nitro compound represented by the following formula (A) in the presence of a metal catalyst and a basic compound, wherein the nitro compound is present in a composition which also contains a compound having a haloarene skeleton when the nitro compound is reduced:

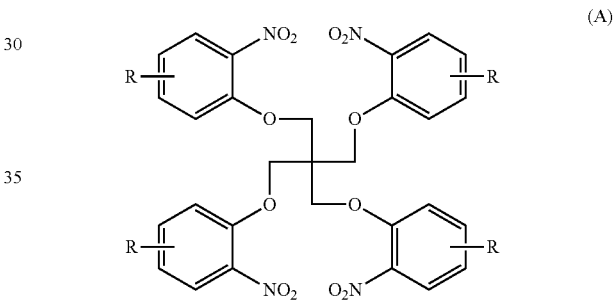

wherein R is a hydrogen atom or an alkyl group having 1 to 6 carbon atoms;

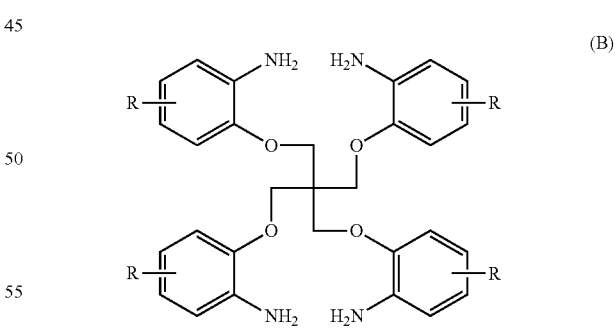

wherein R is as defined in the above formula (A).

2. The production process according to claim 1, wherein the metal catalyst is at least one selected from the group consisting of palladium, ruthenium, platinum, rhodium, nickel, copper, metal oxides thereof, metal hydroxides thereof and metal-supported catalysts obtained by precipitating any one of them on a carrier selected from activated carbon, alumina, titania and silica.

3. The production process according to 1, wherein the basic compound is triethylamine.

4. A process for producing a thiourea compound represented by the following formula (C), comprising the step of reacting the amine compound represented by the formula (B) and obtained by the process of claim 1 with carbon disulfide in the presence of imidazole:

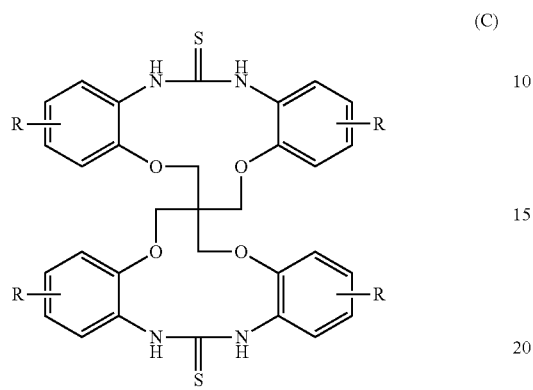

(C)

wherein R is a hydrogen atom or an alkyl group having 1 to 6 carbon atoms.

5. The production process according to claim 4, wherein methyl ethyl ketone is used as a reaction solvent.

\* \* \* \* \*